United States Patent
Sundaram et al.

(10) Patent No.: US 8,445,438 B2
(45) Date of Patent: May 21, 2013

(54) COMPOSITIONS COMPRISING CAPTURE PEPTIDES FOR A β-AMYLOID PEPTIDE

(75) Inventors: Pazhani Sundaram, Cheshire, CT (US); Ranjini K. Sundaram, Cheshire, CT (US)

(73) Assignee: Recombinant Technologies LLC, Cheshire, CT (US)

( * ) Notice: Subject to any disclaimer, the term of this patent is extended or adjusted under 35 U.S.C. 154(b) by 173 days.

(21) Appl. No.: 13/121,709

(22) PCT Filed: Oct. 27, 2009

(86) PCT No.: PCT/US2009/062141
§ 371 (c)(1),
(2), (4) Date: Mar. 31, 2011

(87) PCT Pub. No.: WO2010/062570
PCT Pub. Date: Jun. 3, 2010

(65) Prior Publication Data
US 2011/0189290 A1 Aug. 4, 2011

Related U.S. Application Data

(60) Provisional application No. 61/193,075, filed on Oct. 27, 2008.

(51) Int. Cl.
*A61K 38/00* (2006.01)
*A61P 25/28* (2006.01)
(52) U.S. Cl.
USPC ....................................................... 514/17.8
(58) Field of Classification Search
None
See application file for complete search history.

(56) References Cited

U.S. PATENT DOCUMENTS 6,462,171 B1 * 10/2002 Soto-Jara et al. ............. 530/326

OTHER PUBLICATIONS

International Search Report and Written Opinion; International Application No. PCT/US2009/062141; International Filing Date Oct. 27, 2009; Date of Mailing Jul. 13, 2010; 14 pages.
Kurihara et al.; "Ab1-40 Peptide Radiopharmaceuticals for Brain Amyloid Imaging: In Chelation, Conjugation to Poly(ethylene glycol)-Biotin Linkers, and Autoradiography with Alzheimer's Disease Brain Sections"; Bioconjugate Chem.; 11; pp. 380-386; (2000).
Roberts, et al.; "Chemistry for Peptide and Protein PEGylation"; Advanced Drug Delivery Reviews; 54; pp. 459-476; (2002).
Rocha et al.; "Design and Biological Activity of B-sheet Breaker Peptide Conjugates"; Biochemical and Biophysical Research Communications; 380; pp. 397-401; (2009).
Sato, et al.; "Inhibitors of Amyloid Toxicity Based on B-sheet Packing of AB40 and AB42"; Biochemistry; 45(17; pp. 5503-5516; (2006).
Soto, et al.; "B-sheet Breaker Peptides Inhibit Fibrillogenesis in a Rat Brain Model of Amyloidosis: Implications for Alzheimer's Therapy"; Nature Medicine; 4; No. 7; pp. 822-826; (1998).
Wiesehan, et al.; "Selection of D-Amino-Acid Peptides That Bind to Alzheimer's Disease Amyloid Peptide AB1-42 by Mirror Image Phage Display"; ChemBioChem; 4; pp. 748-753; (2003).

* cited by examiner

*Primary Examiner* — Thomas Heard
(74) *Attorney, Agent, or Firm* — Cantor Colburn LLP

(57) ABSTRACT

Disclosed herein is a composition for the treatment and/or prevention of Alzheimer's disease and the delivery thereof. The composition comprises a PEG hydrogel having bound thereto a capture peptide, wherein the capture peptide is capable of binding beta-amyloid. In another embodiment, the capture peptide is attached to a solid support.

10 Claims, 1 Drawing Sheet

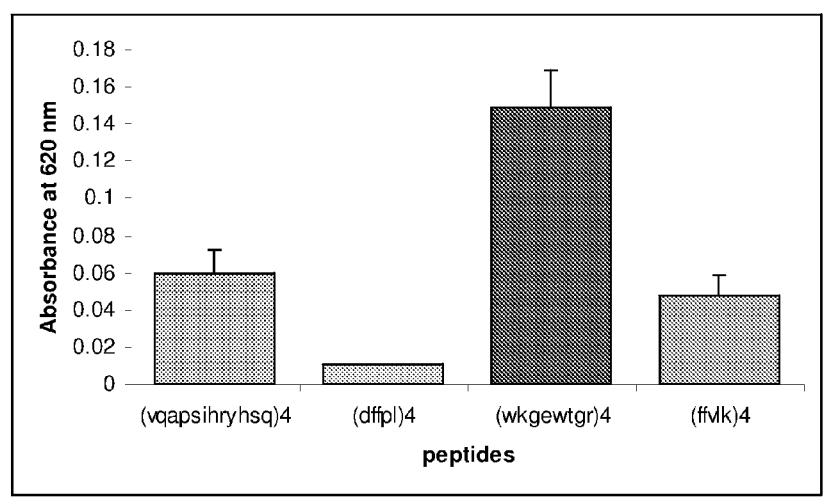

COMPOSITIONS COMPRISING CAPTURE PEPTIDES FOR A β-AMYLOID PEPTIDE

CROSS-REFERENCE TO RELATED APPLICATIONS

This application is a 371 of PCT/US2009/062141, filed on Oct. 27, 2009, which claims priority to U.S. Provisional Application 61/193,075, filed on Oct. 27, 2008, under the provisions of 35 U.S.C. 119 and the International Convention for the Protection of Industrial Property, which is incorporated by reference herein in its entirety

BACKGROUND

The hallmark of Alzheimer's disease (AD) is the presence of senile plaques in the brain, which are composed of a central deposition of β-amyloid peptide. Deposits of β-amyloid peptide play an important role in the pathogenesis of AD as shown by genetic, neuropathological, and biochemical evidence. β-Amyloid (Aβ) peptide is a 39-43 amino acid peptide derived from the amyloid precursor protein (APP) by proteolytic processing. Both $A\beta^{1-40}$ and $A\beta^{1-42}$ are components of the deposits of amyloid fibrils found in brain tissue of AD patients. The aggregation of monomeric Aβ peptides into toxic fibrils and plaques has a rate-limiting nucleation phase followed by rapid extension. $A\beta^{1-42}$ is believed to play a more important role in the early nucleation stage, thus being more "amyloidogenic" than $A\beta^{1-40}$.

Short peptides and small molecules can influence the structure and aggregation of Aβ, and these are effective neuroprotective agents. Peptides that are partially homologous to the central hydrophobic region of Aβ (residues 17-21), but that contain amino acids that prevent the adoption of Aβ-sheet structure bind to Aβ and inhibit amyloid formation in vitro and disaggregate preformed Aβ fibrils. One such analog is the LPFFD peptide that has significant effects on the higher-order structure of Aβ in a shorter time domain than that in which the β-sheet-breaking effect appears, and this has implications for their protective effect. Another such peptide is the analog of the GxxxG motif of the Aβ at residues 25-29. Approaches have targeted Aβ utilizing peptides based on the GxFxGxF scaffold expected to interact with the C terminus of Aβ. The most active compound RGTWEGKW was shown to inhibit fibril formation and reduce cellular toxicity. The Alternating hydrophilic-hydrophobic nature of this peptide may help to disrupt Aβ aggregation.

The mechanism by which natural protein ligands interact with Aβ and reduce its toxicity in the cellular environment is still not clearly understood. Numerous experiments have been conducted to determine possible natural protein binding partners of Aβ. Some of these natural ligands may be a missing link between Aβ accumulation and cellular toxicity.

What is needed are improved compositions for the delivery of peptide ligands that interact with Aβ and can reduce its toxicity in the cellular environment.

SUMMARY

In one embodiment, a composition comprises a poly(ethylene glycol) hydrogel having bound thereto a capture peptide for a β-amyloid peptide, wherein the capture peptide for the β-amyloid peptide is selected from the group consisting of a native, retro or retro-inverso form of FNNGNLFIL (SEQ ID NO:1), LPFFD (SEQ ID NO:1), RGTWEGKW (SEQ ID NO:5), and QSHYRHISPAQV (SEQ ID NO:7).

In another embodiment, a method of treatment of a patient with Alzheimer's disease comprises administering subcutaneously, intradermally or transdermally the composition described above.

In yet another embodiment, a method of treatment of a patient with Alzheimer's disease comprises administering externally to the human body a capture peptide for a β-amyloid peptide immobilized on a solid support, wherein the capture peptide for the β-amyloid peptide is selected from the group consisting of a native, retro or retro-inverso form of FNNGNLFIL (SEQ ID NO:3), LPFFD (SEQ ID NO:1), RGTWEGKW (SEQ ID NO:5), and QSHYRHISPAQV (SEQ ID NO:7).

BRIEF DESCRIPTION OF THE DRAWINGS

FIG. 1 shows the binding capacity of AMYTRAP constructs to Aβ. Values are expressed as mean±SD.

DETAILED DESCRIPTION

Disclosed herein are compositions comprising a poly(ethylene glycol) hydrogels (PEG) having bound thereto a capture peptide for a β-amyloid peptide. In one embodiment, the PEG is cross-linked PEG. In another embodiment, bound means noncovalently or covalently bound, specifically covalently bound. In another embodiment, the capture peptides are bound to a solid support such as a medical prosthesis (e.g., a stent or hemodialysis instrument).

In one embodiment, the capture peptide is attached directly to the poly(ethylene glycol) hydrogel, specifically via reactive groups in the PEG and the capture peptide. In another embodiment, the capture peptide is attached to the poly(ethylene glycol) hydrogel though a carrier molecule such as a carrier protein. In one embodiment, multiple copies of the capture peptide are conjugated to the poly(ethylene glycol) hydrogel through a linker such as a carrier molecule or carrier polypeptide. The capture peptide for a β-amyloid peptide is selected from the group consisting of a native, retro or retro-inverso form of LPFFD (SEQ ID NO:1), FNNGNLFIL (SEQ ID NO:3), RGTWEGKW (SEQ ID NO:5), and QSHYRHISPAQV (SEQ ID NO:7). Such compositions are referred to herein as AMYTRAP. In one embodiment, the AMYTRAP is expected to autodegrade in the liver and excreted by kidneys.

It has been suggested that that Aβ peptides can cross the blood-brain barrier (BBB) and therefore will establish an equilibrium of Aβ in the central nervous system (CNS) and the peripheral circulation of the body. Without being held to theory, it is believed that the AMYTRAP compositions described herein will create a trap that will bind Aβ in the periphery. This AMYTRAP binding will create a flux of Aβ from brain to cross over the BBB causing Aβ to become trapped in the peripheral circulation of the body. The size of the AMYTRAP will prevent it from entering the brain.

Poly ethylene glycol [PEG] reagents are useful for coupling to functional groups of biologically active agents such as proteins, antibody fragments, aptamers, peptides, and small molecules. The chemical attachment of PEG to these biologically active agents is referred to as "PEGylation." PEGylation reaction conditions vary depending on the biological active, the desired site and degree of PEGylation, and the PEG reagent. PEGylation is a proven technology with several FDA-approved products that have created over $5 billion in revenues worldwide. Advanced PEG modification of therapeutics can have the following characteristics: increased in vivo half-life (decreased enzymatic degradation and decreased kidney excretion); enhanced drug performance with reduced immunogenicity, antigenicity and toxicity; and improved physicochemical properties (improved solubility and stability).

Many functionalized forms of the relatively inert polymer, poly (ethylene glycol) (PEG) are commercially available, allowing numerous methods for linking other substances to PEG molecules. Aqueous solutions of the formulation components can be mixed allowing easy and reliable injection. With the versatility provided by the modified forms of PEG, it is possible to covalently attach molecules using bioreversible bonds, such as ester and disulfide bonds. Exemplary PEGs include 4-Arm PEG-NH$_2$ (4 Arm PEG-amine) and 8-Arm PEG-NH$_2$ (4 Arm PEG-amine), 4-Arm PEG-MAL and 4-Arm PEG-NHS.

In one embodiment, the cross-linked PEG is in the form of a hydrogel. Suitable hydrogels have a water content of about 10 wt % to about 90 wt % water.

In one embodiment, the PEG hydrogel is formed from a cross-linked PEG-NH$_2$, 8-arm or 4 arm and VS-PEG-NHS or Mal-PEG-NHS as polymer and copolymer, respectively. SH-PEG-SH, served as the linker. The linker links the conjugated PEG 8-arm together and if it was used at a suitable concentration, linking of the 8-arm PEGs is achieved. The molecular weight of the polymer and copolymer can vary between 2 kDa and 20 kDa The AMYTRAP matrix of a poly(ethylene glycol) hydrogel is a colloidal gel that provides good contact with body fluids while being essentially inert. In one embodiment, the composition comprises a matrix of cross-linked poly(ethylene glycol) having covalently attached thereto a capture peptide for a β-amyloid peptide, which can be injected subcutaneously or applied as a trans-dermal patch. The trap is expected to autodegrade in the liver and excreted by kidneys.

The capture polypeptides are bound directly to the poly (ethylene glycol) hydrogel through reactive groups on the PEG and the capture peptide, or are linked through a linker. Suitable linkers include SH-PEG-SH with a molecular weight of 1 kDa to 20 kDA. In one embodiment, the linker comprises linker comprises reactive groups such as maleimide, NHS, NH$_2$ and SH groups.

The AMYTRAP compositions disclosed herein also include a bound capture peptide. The capture peptide for a β-amyloid peptide is selected from the group consisting of a native, retro or retro-inverso form LPFFD (SEQ ID NO:1), FNNGNLFIL (SEQ ID NO:3), RGTWEGKW (SEQ ID NO:5), and QSHYRHISPAQV (SEQ ID NO:7). The native forms (SEQ ID NOs: 1, 3, 5 and 7 are the native peptides containing L-amino acids. Retro-inverso peptides as defined herein are all D-amino acid versions of the peptide, wherein the amino acids are in reverse order. The capture peptides can be linked by their carboxy or amino terminus. In one embodiment, a plurality of capture peptide is in the form of a multimer. Monomer and multimer capture agents are illustrated in Tables 1-4.

TABLE 1

AMYTRAP 1 [LPFFD-related peptides]

| Structure of conjugate | SEQ ID NO: | Copies of peptide |
|---|---|---|
| LPFFD | 1 | 1 (native) |
| dffpl | 2 | 1 (retro-inverso) |

TABLE 1-continued

AMYTRAP 1 [LPFFD-related peptides]

| Structure of conjugate | SEQ ID NO: | Copies of peptide |
|---|---|---|
| dffpl-βAla \\ lys-cys / dffpl-βAla | | 2 (retro-inverso) |
| dffpl-βAla dffpl-βAla \\ lys$_2$-lys-cys dffpl-βAla / dffpl-βAla | | 4 (retro-inverso) |

TABLE 2

AMYTRAP 2 [FNNGNLFIL-related peptides]

| Structure of conjugate | SEQ ID NO | Copies of peptide |
|---|---|---|
| FNNGNLFIL | 3 | 1 (native) |
| liflngnnf | 4 | 1 (retro-inverso) |
| liflngnnf-βAla \\ lys-cys / liflngnnf-βAla | | 2 (retro-inverso) |
| liflngnnf-βAla liflngnnf-βAla \\ lys$_2$-lys-cys liflngnnf-βAla / liflngnnf-βAla | | 4 (retro-inverso) |

TABLE 3

AMYTRAP 3 [RGTWEGKW-related peptides]

| Structure of conjugate | SEQ ID NO: | Copies of peptide |
|---|---|---|
| RGTWEGKW | 5 | 1 (native) |
| wkgewtgr | 6 | 1 (retro-inverso) |
| wkgewtgr-βAla \\ lys-cys / wkgewtgr-βAla | | 2 (retro-inverso) |
| wkgewtgr-βAla wkgewtgr-βAla \\ lys$_2$-lys-cys wkgewtgr-βAla / wkgewtgr-βAla | | 4 (retro-inverso) |

TABLE 4

AMYTRAP 4 [qshyrhispaqv-related peptides]

| Structure of conjugate | SEQ ID NO: | Copies of peptide |
|---|---|---|
| qshyrhispaq | 7 | 1 (native) |
| vqapsihryhsq | 8 | 1 (retro-inverso) |
| vqapsihryhsq-βAla \<br>                lys-cys<br>vqapsihryhsq-βAla / | | 2 (retro-inverso) |
| vqapsihryhsq-βAla \<br>vqapsihryhsq-βAla \<br>             lys$_2$-lys-cys<br>vqapsihryhsq-βAla /<br>vqapsihryhsq-βAla | | 4 (retro-inverso) |

Lower case is for D-amino acids. βAla is beta-alanine, C-terminus is amidated, uncharged form, N-terminus is free, positive charged form, PEG can be terminated by an amino group at one end and a carboxylate group at the other end. In one embodiment, the cysteine residue is linked via its side chain thiol to the gel matrix. All peptide constructs can be synthesized by solid phase by Fmoc chemistry.

In one embodiment, a carrier molecule is attached to 2-3 arms of the 8-arm PEG. Then the PEG-peptide is reacted with VS-PEG-NHS and the gel is made with the linker, SH-PEG-SH. The vinyl sulfone (VS) group has desirable properties of rapid and selective reaction with thiol (—SH) groups and stability in water, both at neutral pH. The capture reagent such as a peptide composed of D-amino acids is then added. In one embodiment, a Cys is placed at the C-terminus of the peptides to utilize its thiol group for linkage. The cysteine thiol group is used for appending the peptide to the gel matrix. The strategy is used to place the capture peptide at the end of a long PEG chain, thereby allowing it freedom of motion within the hydrogel, which can be greater than 90% water. As a result, the capture peptide should be able to form the multimeric aggregates suitable for high affinity binding of toxic amyloid peptides. Positive and negative control gels are made the same way by replacing the capture peptide with native or scrambled peptides.

In one embodiment, the capture peptide is attached to the PEG via a carrier protein. Exemplary carrier proteins include albumin and transferrin. In one embodiment, lysine residues in the carrier protein are activated with SPDP (N-succinimidyl 3-(2-pyridyldithio)propionate a crosslinker).

Serum albumin is the most abundant protein in blood, and it has a wide range of potential pharmaceutical applications. It serves in different capacities to chemically protect the RES from toxic chemicals, and it is turned over in a half-time of about 19 days. One of its notable properties is accumulation in tumors. Albumin is currently being evaluated as a carrier for use in cancer chemotherapy in human clinical trials.

Without being held to theory, the steps involved in plaque formation and the proposed mechanism of action of "AMYTRAP" are as follows:

STEP 1. APP is produced in the brain

STEP 2. APP is degraded into fragments; the two fragments known as $A\beta^{1-42}$ and $A\beta^{1-40}$ are potentially neurotoxic when they form aggregates.

STEP 3. Under normal circumstances, the rate of production of beta amyloid is equal to its rate of removal from the central nervous system. In AD the rate of removal is less than the rate of production and excess beta amyloid forms plaque.

STEP 4. Administration of AMYTRAP in the periphery will augment the rate of removal of beta amyloid from the CNS, thereby halting plaque formation.

Also included are pharmaceutical formulations comprising an AMYTRAP composition as described herein and a pharmaceutically acceptable excipient. AMYTRAP formulations can be administered subcutaneously, intradermally or transdermally. A pharmaceutical formulation is administered to an Alzheimer's disease patient for the purpose of extracting and accumulating neurotoxic beta-amyloid peptides from body fluids. The formulations can be administered therapeutically or prophylactically. In one embodiment, the pharmaceutical composition is injected inside an Alzheimer's disease patient for the purpose of trapping the beta-amyloid peptides from body fluids. By doing this, the trap will act as a "bait." By drawing beta-amyloid peptide across the blood-brain barrier, it should reduce the concentration of soluble beta-amyloid peptide in the brain, thereby halting or slowing plaque deposition in the brain. Since plaques are the cause of nerve damage in AD, this trapping process is expected to be therapeutically effective.

In another embodiment, an implanted composition (referred to as a trap) is removed after it is no longer functional. The gel may simply be surgically removed or it may be constructed to autodegrade. As a precaution, the trap may also be loaded with a protease or peptidase that will degrade captured beta-amyloid peptide into nontoxic fragments. Alternatively, fragments of the trap or capture peptide may be designed to help eliminate beta-amyloid peptide from the body via the liver. An attribute of the retro-inverso peptides is that the aggregates formed with Aβ peptides are expected to have low toxicity. Dimers and higher order repeats of the binding peptides might require only one attachment site to the matrix or may just be physically trapped in the trap, which might be helpful for their elimination from the body.

In one embodiment, the AMYTRAP is immobilized on a solid support such as a column or a capillary tube. In this embodiment, it is possible to use the support in a hemodialysis system and to deplete the Aβ peptide outside of the body.

The invention is further illustrated by the following examples:

EXAMPLES

Example 1

Strategies Used for Preparation of Gels conjugate I: peptide cross-linked PEG (stationary trap, positive control for therapeutic effect), conjugate II: peptide linked to soluble PEG (soluble mobile trap), conjugate III: Peptide linked to serum albumin and PEG (mobile trap, test sample having both therapeutic effect and elimination from the body).

Polymer PEG (MAL)$_8$ with a molecular weight of 5,000 and 3,400 respectively is available commercially from NOF corp. For the AMYTRAP gels, the capture peptide is attached to 8-n arms of the 8-arm PEG. The binding element, capture peptide (ATP), will be composed of D-amino acids. A "Cys" is incorporated at the C-terminus of the peptides to utilize the Cys thiol group for linkage of the capture peptides to the PEG matrix. The strategy places the capture peptide at the end of a long PEG chain, thereby allowing it freedom of motion within the hydrogel, which is greater than 90% water. As a result, the AMYTRAP should be able to form the multimeric aggregates needed for high affinity binding of toxic amyloid peptides. In one embodiment, the crosslinked PEG matrix is formed in a 2-step procedure by the random reaction of the thiol groups in the cross-linker with the maleimide groups in an 8-arm PEG, forming a network of cross-linked PEGs interspersed with covalently bound binding peptides. The appropriate amounts of each component are added, and all reactions proceed spontaneously due to the use of these preactivated peptides, as follows:

PEG-(maleimide)$_8$+RI-SH (1 to 7 molecules)--> PEG--(maleimide)$_{8-(1\ to\ 7)}$(RI)$_{(1\ to\ 7)}$ PEG--(maleimide)$_{8-(1\ to\ 7)}$(RI)$_{(1\ to\ 7)}$+SH-PEG-SH--> hydrogel having an average of "n" copies of RI     conjugate I RI is a retro-inverso capture polypeptide.

Alternatively, VS-PEG-NHS can also be used as follows:

For 3% gel, approximately 1.5×10−6 moles of PEG was used. VS-PEG-NHS at 1.2-fold molar ratio was added to PEG 8-arm solution very slowly (drop-wise) and mixed by light shaking and left at room temperature for 2 hours for reaction to be complete. This reaction produced PEG-VS8, which was distributed into 1.5 ml polypropylene tubes. Then for detox gels, 4×10−7 moles of respective peptide per gel was added to appropriate tubes and the reaction allowed to go for 6 hours. This way, they were attached to 2-3 arms of the 8-arm PEG. At this point we had PEG-Peptide3-VS5. For empty (control) gel, PB (20 mM, pH=8.0) was used. Reaction was allowed to proceed for 2-12 hours. For the last step linker was added. 3.25×10−7 moles of "disulfide-linker" (HS-PEG 3,400-SH) was added to each tube and mixed to form the gels. This compound will be injected as soon as it is mixed.

The peptides will be purified by reverse-phase HPLC and analyzed by MALDI-TOF to confirm structure. For preparation of the stationary detoxification trap, the matrix-forming constituent will be prepared from an 8-arm form of PEG (commercially available), in which each arm is terminated in a maleimide group. Note: the reactive groups are printed in italics. Reaction with peptide would be via the thiol group on the cysteine residue, as follows:

PEG-(maleimide)$_8$+RI-SH-->PEG-(RI)$_8$     conjugate II

The albumin carrier comprises about 60 lysine residues, of which only a fraction are highly reactive. A prior art process will be employed to generate conjugates having a low (1-3), medium (4-8) or high (9-13) copy number (n) of RIP bound per carrier molecule. The synthetic process includes reaction of lysine amino groups using with the N-hydroxysuccinimde (NHS) group of a bifunctional cross-linker, followed by reaction of the cysteine thiol group in RIP with the maleimide (mal) group of that same reagent. Both reactions may be done in physiological buffer (e.g. phosphate buffer at pH 7). Structures of intermediates and products will be confirmed by various techniques, such as: MALDI-TOF, electrophoresis, amino acid analysis.

albumin[-NH$_2$]$_{60}$+$n$NHS-PEG-mal-->albumin [-NH$_2$]$_{60-n}$[—NH-PEG-mal]$_n$ albumin[-NH$_2$]$_{60-n}$[—NH-PEG-mal]$_n$+peptide-SH--> lbumin[-NH$_2$]$_{60-n}$[—NH-PEG-S-RI]$_n$     conjugate III Albumin used for injections are 99.99% pure and endotoxin free. The solutions are all filter sterilized and we do not expect to get any undesirable immune response from the albumin.

Example 2

In Vitro Testing of AMYTRAP Constructs 200 pg of each peptide was coated on ELISA plates in triplicates. The plates were then incubated at 37° C. overnight, and blocked with a solution containing 3% gelatin in 1× Tris-buffered saline for 2 h at room temperature. 10 ng of Aβ-42 was then added to each peptide-coated wells and incubated for 2 h at room temperature. After washing with 0.1% Tween 20 in Tris-buffered saline, plates were incubated with anti Aβ B-42 antibody for one hour (biotin labelled 4G8 monoclonal antibody from Covance). Following this incubation, the plates were washed and incubated with HRP-labeled goat anti-mouse secondary antibodies (Kirkegaard and Perry, Gaithersburg, Md. at 1:5000 dilution) for 2 hours at room temperature. They were again washed with TBST and HRP substrate solution (Kirkegaard and Perry, Gaithersburg, Md.) was added following which absorbance was read at 620 nm. Values are expressed as mean±SD. As can be seen in FIG. 1, we have identified two peptides that have better binding capacities than LPFFD (SEQ ID NO:9) in an invitro assay.

Example 3

Test and Compare the Efficacies of Different Hydrogels in a Mouse Model of AD

Study Design and Expertise. All injection materials will be prepared in a BL2 hood. All solutions will be filter sterilized and endotoxin free. Gel solutions will be injected under our supervision using Taconic Farms' animal protocols. Their scientists will provide assistance with injecting and sacrificing mice under our supervision. This is to make sure reasonable and appropriate measures are taken during the study to give us confidence in the safety of our gels Animal Model. Alzheimer's disease mouse model, [APP Microinjected Mouse Model (Human β-Amyloid Precursor Protein Expresser) available with Taconic Farms will be used in the present study. The APPSWE (2576) mouse model carries a transgene coding for the 695-amino acid isoform of human Alzheimer β-amyloid (Aβ) precursor protein derived from a large Swedish family with early-onset Alzheimer's disease (AD). The mouse expresses high concentrations of the mutant Aβ, develops significant amyloid plaques, and displays memory deficits. The elevated Aβ levels are associated with the development of amyloid deposits in frontal, temporal, and entorhinal cortex, hippocampus, presubiculum, subiculum, and cerebellum. Some mice even develop the signature "Maltese cross" pattern of amyloid deposits seen in human AD. Memory deficits have been demonstrated in 9-10 month old transgenic mice via altered performance in Y maze test, which is one of the standard memory and learning tests for mice. The APPSWE (2576) mouse model shows many similarities to human AD and provides the opportunity to study drugs designed for treatment or prevention of AD.

Candidate conjugates will be evaluated in the above mouse model. We will have 6 groups of mice in our study. Group 2-5 will have 12 mice each that will be injected with AMYTRAP gel 1 (wkgewtg)$^4$ through and AMYTRAP gel 4 (vqapsihryhsq)$^4$ respectively.

Group 6 will be the control gel (ffvlk)$^4$. Group 1 will be the control group where mice will be injected with gel alone. Mice will be sacrificed periodically as described in Table 1. Mice at about 7 months of age will be used. Whole mouse necropsy studies will also be performed.

TABLE 5

INJECTION SCHEDULE

| Group | | | | |
|---|---|---|---|---|
| Group 1 (Hydrogel alone) 12 mice | Y maze day 0 | Inject detox gel on day 1, 28, 56, 112 and 168 | Y maze on day 170 | Euthanize on day 171. |
| Group 2 (Hydrogel with [wkgewtg]⁴ peptide) 12 mice | Y maze day 0 | Inject detox gel on day 1, 28, 56, 112 and 168 | Y maze on day 170 | Euthanize on day 171. |
| Group 3 (Hydrogel with [vqapsihryhsq]⁴ peptide) 12 mice | Y maze day 0 | Inject detox gel on day 1, 28, 56, 112 and 168 | Y maze on day 170 | Euthanize on day 171. |
| Group 4 (Hydrogel with [liflngnnf]⁴ peptide) 12 mice | Y maze day 0 | Inject detox gel on day 1, 28, 56, 112 and 168 | Y maze on day 170 | Euthanize on day 171. |
| Group 5 (Hydrogel with [dffpl]⁴ peptide) 12 mice | Y maze day 0 | Inject detox gel on day 1, 28, 56, 112 and 168 | Y maze on day 170 | Euthanize on day 171. |
| Group 6 (Hydrogel with [ffvlk]⁴ peptide) 12 mice | Y maze day 0 | Inject detox gel on day 1, 28, 56, 112 and 168 | Y maze on day 170 | Euthanize on day 171. |

Behavioral testing—Y Maze. Briefly, handle mice gently, holding by tail and let rest on arm, taking care not to let mouse plunge down head first into maze. Mice are individually placed in the center of a Y maze, with all three arms available for exploration, for a period of 8 minutes. The Y maze is a three-arm maze with equal angles between all arms. Mice will be initially placed within one arm, and the sequence and number of arm entries will be recorded for each mouse over an 8 min period. The percentage of triads in which all three arms are represented will be recorded as an alternation to estimate short-term memory of the last arms entered. After the test, transfer data from hard copy to Excel spreadsheet. An alternation is defined as a visit to all three arms without re-entry (ABC, ACB, BAC, BCA, CAB or CBA). Analyze each ARM ENTRY separately and determine whether it completed an alternation. The sequence ABCABC has four alternations, the first ends with C, the next with A, then B, then C. The sequence ABCBAC has only three alternations, the first ending in C, the second ending with A, and the third with C. % alternations is (number of observed alternations)/(number of possible alternations). If n arms are visited, the highest possible number of alternations is n−2. If the animal moves randomly, 22% alternations would be expected (3*2*1/3*3*3). Global activity is reflected in the total number of visits to the different arms. ACTIVITY is therefore (total number of arm entries)/minutes of observation).

Radial arm maze test. Cognitive tests will be performed using a black, wooden 8-arm radial maze. The maze will be elevated 30 cm off the floor with a central platform 35 cm in diameter and 8 arms each 10×80 cm. Each arm will contain a food cup, at its terminal end, which will be baited during testing with ½ piece of sweetened cereal (Froot Loops®, Kellogg's, Battle Creek, Mich., USA). Then a 30-cm opaque ring will be placed on the central platform and the mouse will be placed inside the ring for 10 s. After this interval, the ring will be removed and timing started. The mouse will be allowed to run on the maze until all 8 arms will be entered or until 300 s had passed. An arm entry will be recorded when all four of the animal's legs had crossed the threshold of the arm. Choice accuracy will be measured by entries to repeat (ETR), which will be the number of arms entered until a repeat entry will be made in a previously chosen arm. For the session to be included in the analysis, the mouse had to either have a repeated entry, finish the maze perfectly with no repeated entries, or have chosen more than half of the arms before the end of the session. Response latency will be recorded as the total time divided by the number of arm entries. The square root transformation will be used to reduce the heterogeneity of variance in latency measurements. The mice will be trained 4-5 days per week.

Animal Safety. Considering safety and tissue reactions, several excised gels and surrounding tissue will be placed in formalin for a pathology report. Periodically, the body weight of each mouse will be measured, and the average body weight within each experimental group will be compared to a group of 6 control mice. Any adverse events in an experimental group, such as death, paralysis, weight loss, etc., will be recorded. Premature mortality is an expected phenotype of the APP Microinjected Mouse. Mortality of >20% is anticipated, particularly in male APP mice. We will take this into consideration and adjust the order number to retain the needed group sizes.

Example 4

Medicated Prosthesis

In another embodiment, a medical prosthesis, such as a stent or hemodialysis instrument, which is loaded with irreversibly bound capture peptides, is also included. Peptides will be synthesized with six histidine residues on the C terminus as shown in FIGURE. Purified peptides will be dissolved in 1 mL of 0.1 M tricine buffer (pH 8.0) to a final concentration of 100 μM. Nickel chloride will be added to peptide solution to a final concentration of 100 μM. The $Ni^{2+}$ coordinated hexahistidine peptide will be employed in the subsequent experiments. A platinum micro-disk electrode (MDE; ID=50 μm) will be employed as the solid substrate for peptide immobilization. The Pt MDE will be connected to a computerized electrochemical polarizer (Hokuto Denko Co., Japan) with a Pt wire electrode as the counter electrode and an Ag/AgCl electrode as the reference electrode. The Pt MDE will be cleaned by immersion in piranha solution (70/30, v/v sulfuric acid and 30% hydrogen peroxide) for 30 min followed by washing in deionized water. In order to prevent non-specific adsorption of peptides to the microelectrode, the microelectrode will be immersed in blocking solution overnight. Cyclic voltametry will be performed on the MDE with potential sweeping from −800 to +800 mV versus Ag/AgCl at scan rate of 200 mV s⁻¹ repeatedly 60 times. Absorbed blocking reagent can be removed from the electrode during the electrochemical potential sweeping. The electrochemical immobilization/removal of the peptide will be controlled by applying a potential to the MDE. After electrochemical immobilization of the peptide, the microelectrode will be will washed in buffer solution with sonication at 100 Hz.

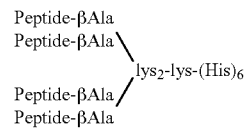

When the stent, for example, is implanted into the blood vessel of a patient, the capture peptides in the stent capture the Aβ from circulation. The stent may be periodically removed and new stents implanted. The stent may be formed from any metal or solid implantable device in the form of a wire, tube, or sheet. Alternatively, a hemodialysis-like setup could be done where the patient's blood is passed through a bio-compatible column/capillary tubing, loaded with immobilized capture peptides. After several passes, the tubing support with retained toxic Aβ peptides are removed from circulation at periodic intervals and replaced with a fresh set up.

Advantages are the disclosed AMYTRAP compositions include the ability to build a scaffold containing many copies of the peptide that will increase binding capacity of the compositions. Also, the use of D enantiomers can further decrease immunogenicity compared to L-enantiomers. The use of use retro-inverse peptides (D enantiomers in reverse order) can also improve the activity of the peptides compared to the native peptides.

By combining the features of the Aβ binding agents with the properties of pegylation, a innovative therapeutic system has been produced. Without being held to theory, it is believed that the AMYTRAP system will be able to accumulate soluble Aβ, preventing its deposition as plaque in the brain, thereby halting progression of Alzheimer's disease. The AMYTRAP composition provides a therapeutic product for treatment of AD.

All methods described herein can be performed in a suitable order unless otherwise indicated or clearly contradicted by context. The use of any and all examples, or exemplary language (e.g., "such as") herein is intended to better illuminate the disclosure and is non-limiting unless otherwise specified. No language in the specification should be construed as indicating that any non-claimed element as essential to the practice of the claimed embodiments. Unless defined otherwise, technical and scientific terms used herein have the same meaning as is commonly understood by one of skill in the art to which this disclosure belongs. The terms wt %, weight percent, percent by weight, etc. are equivalent and interchangeable. The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to").

Embodiments are described herein, including the best modes known to the inventors. Variations of such embodiments will become apparent to those of ordinary skill in the art upon reading the foregoing description. The skilled artisan is expected to employ such variations as appropriate, and the disclosed methods are expected to be practiced otherwise than as specifically described herein. Accordingly, all modifications and equivalents of the subject matter recited in the claims appended hereto are included to the extent permitted by applicable law. Moreover, any combination of the above-described elements in all possible variations thereof is encompassed unless otherwise indicated herein or otherwise clearly contradicted by context.

What is claimed is:

1. A composition comprising a poly(ethylene glycol) hydrogel having bound thereto a capture peptide for a β-amyloid peptide,
wherein the capture peptide for the β-amyloid peptide is selected from the group consisting of a native, retro or retro-inverso form of FNNGNLFIL (SEQ ID NO:3), RGTWEGKW (SEQ ID NO:5), and QSHYRHISPAQV (SEQ ID NO:7).

2. The composition of claim 1, wherein the capture peptide is in the retro-inverso form.

3. The composition of claim 1, wherein the poly(ethylene glycol) is in the form of a hydrogel having a water content of 10 wt % to 90 wt %.

4. The composition of claim 1, wherein the poly (ethylene glycol) is cross-linked poly (ethylene glycol).

5. The composition of claim 4, wherein the cross-linked poly(ethylene glycol) is 4-Arm PEG-NH$_2$, 8-Arm PEG-NH$_2$, 4-Arm PEG-maleimide, or 4-Arm PEG-NHS.

6. The composition of claim 1, wherein the capture peptide is linked to the poly (ethylene glycol) hydrogel through a linker molecule.

7. The composition of claim 6, wherein the linker comprises reactive groups such as maleimide, NHS, NH$_2$ and SH groups.

8. The composition of claim 1, wherein the capture peptide is in the form of a multimer when it is covalently attached to the poly(ethylene glycol).

9. The composition of claim 1, wherein the capture peptide is bound to the poly (ethylene glycol) hydrogel by a carrier molecule that is bound to the poly(ethylene glycol).

10. The composition of claim 9, wherein the carrier molecule is albumin or transferrin.

* * * * *

SEQUENCE LISTING

```
<160> NUMBER OF SEQ ID NOS: 9

<210> SEQ ID NO 1
<211> LENGTH: 5
<212> TYPE: PRT
<213> ORGANISM: Homo sapiens

<400> SEQUENCE: 1

Leu Pro Phe Phe Asp
1               5

<210> SEQ ID NO 2
<211> LENGTH: 5
<212> TYPE: PRT
<213> ORGANISM: Homo sapiens

<400> SEQUENCE: 2

Asp Phe Phe Pro Leu
1               5

<210> SEQ ID NO 3
<211> LENGTH: 9
<212> TYPE: PRT
<213> ORGANISM: Homo sapiens

<400> SEQUENCE: 3

Phe Asn Asn Gly Asn Leu Phe Ile Leu
1               5

<210> SEQ ID NO 4
<211> LENGTH: 9
<212> TYPE: PRT
<213> ORGANISM: Homo sapiens

<400> SEQUENCE: 4

Leu Ile Phe Leu Asn Gly Asn Asn Phe
```

```
<210> SEQ ID NO 5
<211> LENGTH: 8
<212> TYPE: PRT
<213> ORGANISM: Homo sapiens

<400> SEQUENCE: 5

Arg Gly Thr Trp Glu Gly Lys Trp
1               5

<210> SEQ ID NO 6
<211> LENGTH: 8
<212> TYPE: PRT
<213> ORGANISM: Homo sapiens

<400> SEQUENCE: 6

Trp Lys Gly Glu Trp Thr Gly Arg
1               5

<210> SEQ ID NO 7
<211> LENGTH: 11
<212> TYPE: PRT
<213> ORGANISM: Homo sapiens

<400> SEQUENCE: 7

Gln Ser His Tyr Arg His Ile Ser Pro Ala Gln
1               5                   10

<210> SEQ ID NO 8
<211> LENGTH: 12
<212> TYPE: PRT
<213> ORGANISM: Homo sapiens

<400> SEQUENCE: 8

Val Gln Ala Pro Ser Ile His Arg Tyr His Ser Gln
1               5                   10

<210> SEQ ID NO 9
<211> LENGTH: 5
<212> TYPE: PRT
<213> ORGANISM: Homo sapiens

<400> SEQUENCE: 9

Leu Pro Phe Phe Asp
1               5
```